United States Patent [19]

Winston et al.

[11] Patent Number: 4,613,616

[45] Date of Patent: Sep. 23, 1986

[54] POLYMERIC IRON CHELATORS

[75] Inventors: Anthony Winston; D. V. P. R. Varaprasad, both of Morgantown, W. Va.

[73] Assignee: Research Corporation, New York, N.Y.

[21] Appl. No.: 632,763

[22] Filed: Jul. 20, 1984

[51] Int. Cl.[4] .......... C07C 81/04; C02F 1/42; G21F 9/04; B01D 15/04
[52] U.S. Cl. .......... 514/507; 514/563; 514/645; 514/815; 514/836; 260/500.5 H; 210/688; 210/692; 210/912; 210/927
[58] Field of Search .......... 514/507, 563, 645, 814, 514/815, 836; 424/DIG. 6, 1.1; 210/681, 688, 692, 912, 927; 260/500.5 H

[56] References Cited

U.S. PATENT DOCUMENTS 3,154,499 10/1964 Fetscher .......... 424/1.1
3,345,344 10/1967 Fetscher et al. .......... 525/355
4,256,765 3/1981 Munakata et al. .......... 260/500.5 H

OTHER PUBLICATIONS

CA 99:169056c, vol. 99, 1983, Winston et al.

Primary Examiner—John Kight
Assistant Examiner—Nathan M. Nutter
Attorney, Agent, or Firm—Scully, Scott, Murphy & Presser

[57] ABSTRACT

The present invention relates to polymeric iron chelators based upon hydroxamic acids having the general formula:

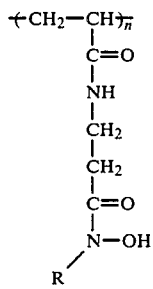

wherein R is hydrogen or lower alkyl. The present compound is useful for the treatment of iron overload disorders particularly arising from iron poisoning and the disease $\beta$-thalassemia otherwise known as Cooley's Anemia. The polymeric hydroxamic acids of the present invention exhibit high selectivity for iron, good water solubility for both the chelator and its iron complex, low toxicity and, most significantly, increased bioactivity, i.e., the ability to remove iron in vivo.

8 Claims, No Drawings

POLYMERIC IRON CHELATORS

BACKGROUND OF THE INVENTION

This invention relates to new iron chelators which are useful in the treatment of acute iron overload disorders, such as, iron poisoning, hemocheomotosis and transfusional hemosiderosis resulting from frequent blood transfusions during the treatment of β-thalassemia otherwise known as Cooley's Anemia, sickle cell anemia, aplastic anemia and some forms of leukemia. More specifically, the present invention contemplates synthetic polymeric iron chelators which are based upon hydroxamic acids having the following general formula:

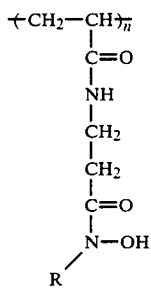

Hydroxamic acids have long been known for their powerful ability to selectively bind iron, Fe(III). Microorganisms have incorporated hydroxamic acids into complex organic molecules for the purpose of scavenging iron from the environment. Since about 1960, desferrioxamine-B (DFB) one of these naturally occurring tris-hydroxamic acids, has been used in medicine to sequester and remove iron from patients with iron overload arising from causes such as iron poisoning and Cooley's Anemia and today many varieties of ferrichromes and ferrioxamines are known and well characterized.

Problems with the use of DFB, however, have resulted in the development of many projects directed to synthesis and evaluation of new iron chelators based on hydroxamic acids and other iron chelating groups. One particular class of iron chelators that appears to be a promising candidate for medical use in the treatment of Cooley's Anemia is a series of water soluble acrylic polymers which bear side chains terminated in hydroxamic acids. The length of the side chains are adjusted to optimize the fit of three neighboring hydroxamic acids about a single iron atom. Such placement retards intermolecular complexation, prevents cross-linking, and ensures that the complexes will be water soluble and, thus, capable of diffusing out of the circulatory system.

Cooley's Anemia is a genetic disorder, rare in the United States, but widely distributed throughout the Mediterranean area, the Middle East, India, and Southeast Asia. The disease, appearing largely in persons with Greek, Italian, or Oriental decent, is characterized by an inability to synthesize adequate amounts of the β-chain of hemoglobin. Since excess α-chains cannot form soluble tetramers, precipitation occurs in the red cell precursors leading to their death and to the condition of anemia.

Because of the inability to synthesize the β-chain of hemoglobin, the only effective treatment of β-thalassemia is to administer blood transfusions throughout life. Such continual transfusions introduce large quantities of iron, which, if not removed, accumulate and form deposits in the liver, spleen, heart, and other vital organs. Death is usually by cardiac failure. To remove iron, the naturally occurring iron chelator, DFB is administered. DFB reduces iron levels by forming a stable soluble iron complex, which is eliminated in the urine and stool.

Iron chelation therapy has therefore become, over the past 20 years, an established method for treating other iron overload conditions as well. Iron poisoning, for example, most often arises in small children through the inadvertant ingestion of iron preparations. Before the introduction of iron chelation therapy in the early 1960's, such conditions were often fatal. Now, through the use of a powerful iron chelator, iron poisonings are treated with a great degree of success.

Although DFB therapy is effective in removing large quantities of iron rapidly, there are some drawbacks in its use. One of these is the short plasma residence time, about 30 minutes, which causes a significant reduction in the efficiency of DFB to remove iron. To counteract this rapid plasma clearance, the chelator is often administered by frequent slow subcutaneous infusion. A portable pump worn by the patient is often used to continuously administer a controlled amount of the drug. On the other hand, the pump is often psychologically unacceptable, and frequent injections throughout the day are painful and not very practical.

The present design of the new iron chelators has been directed largely toward mimicking the naturally occurring siderophores, such as desferrioxamine and ferrichrome, by inclusion of hydroxamic acids into a variety of structures in order to produce compounds having exceptionally high stability constants for iron, close to, or higher than that or DFB.

Besides an affinity for iron, several other criteria are required for an iron chelator to be considered for use in iron chelation therapy; high selectivity for iron, good water solubility of both the chelator and its iron complex, ability of the chelator to remove iron in vivo, and low toxicity.

A frequent approach to the development of iron chelators for medical applications, is to synthesize a series of polymers based on hydroxamic acids (HA). Hydroxamic acids are chosen as the functional group most likely to prove medically successful because of the long and extensive clinical use of DFB. The polymer would serve as a framework to hold the hydroxamic acids in close proximity to another, a feature designed to promote chelation and to ensure high stability constants of the iron complexes. It is also believed that perhaps the polymeric nature of these materials would extend the lifetime of the chelator in the plasma and thus improve chelator efficiency for iron removal.

Although several polymeric compounds with side chains terminating in hydroxamic acids have been synthesized and, to varying extents, have been shown to successfully mimick the iron chelating behavior of the naturally occuring ferroxamines, the novel iron chelating compounds of the present invention surprisingly exhibit improved stability and increased bioactivity relative to compounds presently known.

SUMMARY OF THE INVENTION

It is therefore one object of the present invention to provide a novel polymeric iron chelator which is useful in the treatment of acute iron overload disorders.

It is another object of this invention to provide a polymeric iron chelator which exhibits increased plasma residence time.

A further object of the present invention is to provide a polymeric iron chelator which exhibits increased affinity for iron, good water solubility for the chelator and its iron complex, increased bioactivity and low toxicity.

Still another object of this invention is to provide a method of treatment for acute iron overload disorders including iron poisoning, hemochromotosis and transfusional hemosiderosis resulting from frequent blood transfusions during the treatment of Cooley's Anemia, sickle cell anemia, aplastic anemia and some forms of leukemia.

These and other objects of the present invention are achieved herein by employing a polymeric iron chelator based upon hydroxamic acids having the general formula:

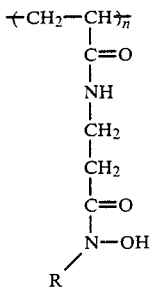

wherein R is hydrogen or lower alkyl, preferably methyl, and n is about 40 to about 300 or more.

The novel chelating compounds of the present invention exhibit high selectivity for iron, good water solubility of both the chelator and its iron complex, low toxicity and, most significantly, increased bioactivity relative to DFB and many other iron chelating compositions presently known.

Moreover, the polymeric iron chelating compounds of this invention can be employed in the treatment of acute iron overload disorders such as iron poisoning, hemochromotosis and transfusional hemosiderosis resulting from frequent blood transfusions during the treatment of Cooley's Anemia, sickle cell anemia, aplastic anemia and some forms of leukemia. By the administration of the present chelating compounds in amounts sufficient to effect (a) the formation of a stable iron complex in vivo and (b) the metabolic elimination of excess iron from the plasma of the affected subject, the aforementioned disorders can be more successfully treated than with other conventional iron chelating compounds. In fact, the compounds of the present invention exhibit up to three and one-half times the efficacy than observed using other known compounds and can be employed in the treatment of human and animal disorders.

BRIEF DESCRIPTION OF THE DRAWINGS

FIGS. 1-17 depict the structural and numbering scheme for the polymeric hydroxamic acids of the present invention and their polymer precursors.

DETAILED DESCRIPTION OF THE INVENTION

In accordance with the present invention, polymeric iron chelators based upon terminating hydroxamic acids having the general formula:

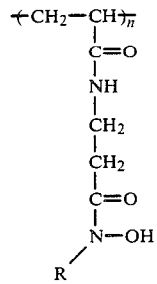

wherein R is hydrogen or lower alkyl, preferably methyl, and is about 40 to about 300 or more, are employed in a method for treating acute iron overload disorders, particularly arising from iron poisoning resulting from the treatment of $\beta$-thalassemia, sickle cell anemia, aplastic anemia and some forms of leukemia.

More specifically, the new polymers of the present invention are derived from acryloyl backbones which bear side chains terminated in hydroxamic acids. Accordingly, it has been determined that the side chain length, which establishes the atomic chain distances between hydroxamic acid groups, has the most pronounced effect on the stability constant ($K_f$) of the iron chelate. It has also been determined herein that this atomic chain distance facilitates the fit of three neighboring hydroxamic acids to the octahedral sphere of the iron atom during binding. The stability of the iron complexes appears to be optimum at an 11-atom spacing between hydroxamic acids (P-valves) and decreases with shorter or longer spacing distances. For example, for a series of three vinyl polymers P-9, P-11 and P-13 in which neighboring hydroxamic acids were separated from each other by 9, 11, and 13 atoms, respectively, it was found that the maximum stability constant of the iron complex was exhibited by polymer P-11, i.e., 11 atom spacing (log K=29.7). The stability constant of the iron complex of P-9, i.e., 9 atom spacing, was an order of magnitude less (log K=28.6) while that for P-13, i.e., 13 atom spacing, was only slighly less (log K=29.4). The spacing between hydroxamic acids of P-11 is therefore believed to be about optimum for formation of the 3:1 iron(III) complex in which three neighboring hydroxamic acids coordinate with a single iron atom in the required octahedral arrangement. The lower stability of the iron complex of P-9 is attributed to a greater degree of strain in forming the octahedral complex due to the shorter side chains. For P-13, the slightly lower stability of the complex is consistent with a greater number of degrees of freedom associated with the longer side chains.

While not wishing to be bound, molecular models indicate that, whereas two neighboring hydroxamic acids could easily bind a single iron, attachment of the third sequential hydroxamic acid to the iron required some strain. This strain is not particularly severe for P-11 and P-13, but in the case of the shorter side chains of P-9, considerable strain is involved in attaching this third hydroxamic acid. The general scheme for the synthesis of the hydroaxamic acid polymers of the present invention is shown in Scheme I, below.

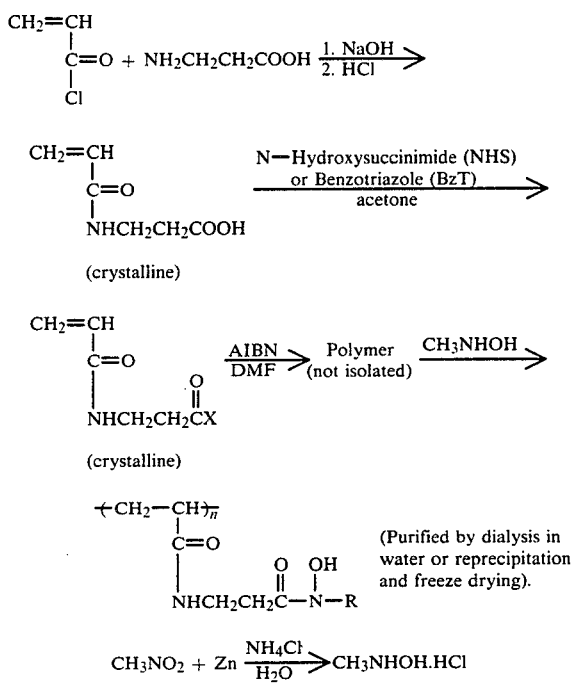

(X is NHS or BzT derivative) (R is hydrogen or methyl)

In accordance with the present invention, several polymers based upon hydroxamic acids were synthesized in accordance with Scheme I. The two new polymers specifically, (poly) N-acryloyl-β-alanine hydroxamic acid and (poly) N-acryloyl-β-alanine-N'-methyl hydroxamic acid (FIGS. 5b and 7b, respectively, demonstrate bioactivity at least three times greater than DFB and the other analogs synthesized. Alanine was specifically employed to provide the preferable spacer units thereby permitting the preferable atomic chain distance of 11 between hydroxamic acid groups.

Generally, the first step in the synthesis of the present compounds is to construct a vinyl monomer bearing a side chain terminated by an active ester that is easily converted to hydroxamic acid. The length of the side chains are such that when polymerized, neighboring hydroxamic acids are preferably separated by 11 atoms which is optimum for iron chelation. Polymerization, followed by conversion of the active ester to hydroxamic acid, affords the final polymer. Preferably, the polymers are readily purified by membrane dialysis, a technique not applicable to non-polymeric materials, although other conventional techniques can be employed.

Although it is not a characteristic of hydroxamic acids, in general, to possess the ability to remove iron in vivo, Tables II and III below clearly indicate that the polymeric hydroxamic acid, of the present invention are reasonably consistent as to this characteristic.

While not wishing to be bound, the evidence demonstrated in accordance with the present invention indicates that polyfunctional hydroxamic acids are situated on the same molecule arranged in such a way to permit cooperation in binding iron. This cooperation is called the "chelate effect" and can increase the normal binding constant ($K_f$) of hydroxamic acid by several orders of magnitude. A high binding constant for iron is, of course, a prime prerequisite for bioactivity.

Molecular weight also appears to be a significant factor. For example, polymers 8bI, 8bII, and 8bIII in the Tables below, which differ in molecular weight, demonstrate increasing activity with increasing molecular weight (about 20,000-50,000 MW based upon viscosity and dialysis data).

The surprising and unexpected increase in bioactivity which is exhibited by the present compounds, i.e., (poly) N-acryloyl-β-alanine hydroxamic acid and (poly) N-acryloyl-β-alanine-N'-methyl hydroxamic acid, is believed to be attributed to the absence of the chain methyl substituent and its positive effect on the hydrophiliclipophilic balance of the polymer. Moreover, it would also appear that the absence of the chain methyl substituent permits increased chain building during polymerization thereby increasing the molecular weight of the molecule and permitting a concomitant increase in bioactivity. Moreover, the present compounds exhibit no toxicity. Although both compounds of this invention are desirable, the N'-methyl acid is preferred.

The spacing distance of the hydroxamic acids from the backbone polymer chain is significant with respect to activity and toxicity. The β-alanine spacer unit is clearly superior to any other variation and is therefore preferred. When the chain is shorter as in the case of glycine and DL-alanine, the activity is less and toxic signs often appear. In the cases where there are no spacing units, e.g., compounds 16 and 17 as shown in the Tables below, not only is the activity low, but the toxicity becomes acute as revealed by several fatalities. In the case of the glutamic acid spacer, as employed in the synthesis of compound 16, which also introduces an additional hydroxamic acid site, considerable toxicity is observed.

The question arises as the cause of this toxicity which appears for some cases but not for others. Toxicity cannot be due to a response to any particular functional group, otherwise all these compounds would be toxic. The structure and arrangement of the polymer itself is of some importance in this regard. It has been determined that when the spacer is short, or non existent, the iron complexes have low solubility and often precipitate out on the addition of just small amounts of iron. On the other hand, when the spacer is longer, e.g., β-alanine, the iron complexes are much more soluble and do not precipitate readily. Clearly this is a result of intra- vs. intermolecular complexation. When the spacing distance is sufficient, the iron forms complexes with the polymer intramolecularly using three neighboring hydroxamic acids to form the octahedral complex, which is then soluble. When the spacing distance is short, there is insufficient chain length to form an intramolecular complex, and hence the complex forms intermolecularly using hydroxamic acids from different chains. The result is a highly crosslinked network polymer which is highly insoluble. Clearly, if the iron, on being complexed in vivo, causes precipitation in the plasma, serious physiological complications would result. The compounds of the present invention exhibit no toxicity while maintaining higher activity than DFB and other known compounds.

As indicated in Table III, activity generally increases with decreasing dose. This effect appears to be generally characteristic of iron chelators and is well established for DFB itself. This effect has been suggested to indicate that the iron becomes available for chelation in the plasma fairly slowly. Thus, at lower doses the chelator works more efficiently to scavenge iron before being lost from the system by other processes.

Hydroxamic acid iron chelators for use in vivo should be designed to possess several hydroxamic acids arranged so that iron chelation can occur intramolecularly to give soluble iron complexes as effected by the present compounds. High molecular weight also appears to be an advantage in a way that extends the total lifetime of the chelator in the plasma and permits a better chelator efficiency. The absence of the chain methyl group contributes to polymerization permitting increased molecular weight which is believed to contribute to the increased residence time observed by the present compounds.

In order to effect treatment of any of the acute iron overload disorders, such as, for example, iron poisoning, hemochromotosis and transfusional hemosiderosis resulting from frequent blood transfusions during the treatment of $\beta$-thalassemia otherwise known as Cooley's Anemia, sickle cell anemia, aplastic anemia, some forms of leukemia, and the like, the compounds of this invention are administered by perenteral means, i.e., intravenus, intramuscular and subcutaneously employing mini pumps or other conventional techniques.

The present polymeric hydroxamic acids can be administered in amounts varying from about 1 to about 5 g per day over the lifetime of the patient, or about 20 to about 40 mg/kg/day. Young children from ages 2 to 5 can receive about 1 g/day while older children from ages 8 to 10 can receive about 2 g/day.

Treatment with the present compounds can remove about 50 to about 100 mg of iron per day while more intensive regimes can remove several hundred mg/day.

In the absence of transfusion-iron chelation therapy, the life expectancy of an afflicted subject is no later than teens. Moreover, in the absence of such therapy, excess iron from transfusions forms deposits in the liver, spleen, heart and other vital organs. In these cases, patients often succumb to cardiac failure. With a regime of transfusions and iron chelation therapy, the lifespan can be extended into the forties.

For a better understanding of the present invention together with other and further objects, reference is made to the following descriptions and examples.

EXAMPLES

Methods

In a general procedure for preparing acryloyl and methacryloyl derivatives of amino acids, acryloyl or methacryloyl chloride was added with vigorous stirring to a solution of the amino acid in aqueous sodium hydroxide. During the addition, the temperature was maintained below 5° C. by means of an ice bath. After the addition was complete, the mixture was stirred for 10–13 minutes and then acidified with conc. HCl to a pH of 2. In the case of DL- and L-alanines and N-acryloyl-$\beta$-alanine, the solid product precipitated on acidification and was collected by filtration. In other cases, the product was isolated by extraction with chloroform or ethyl acetate followed by evaporation.

In a general procedure for preparing N-hydroxysuccinimide esters, a solution of equivalent amounts of the acid and N-hydroxysuccinimide in dry dioxane was treated with dicyclohexylcarbodimide with cooling to 15° C. After 6 hours the dicyclohexylurea was removed by filtration and the solution was concentrated under reduced pressure. Addition of ether or petroleum ether caused the product to precipitate as fine crystals. The product may be recrystallized from ethyl acetate or dioxane-ether.

In a general procedure for polymerization and conversion to the hydroxamic acid polymers, polymerizations may be conducted in dimethylformamide (DMF), N-methylpyrollidone (NMP), or dimethyl sulfoxide, although the latter solvent is not recommended. Dioxane may also be used, but the polymers are generally insoluble in this solvent and precipitate out on polymerization. In this event, the polymer is redissolved in DMF or NMP.

The solution of the monomer is purged with oxygen-free dry nitrogen. The initiator, azobisisobutyronitrile (about 1%) is added and the reaction mixture is heated at 60°–70° C. for a period of from 2 to 7 days. Additional initiator is sometimes added over the course of the polymerization. After polymerization, the reaction mixture is treated directly with excess hydroxylamine or methylhydroxylamine. Hydroxylamine and methylhydroxylamine are prepared from the corresponding hydrochlorides through reaction with triethylamine (TEA) followed by filtration of the TEA·HCl. The hydroxylamine is added to the DMF or NMP solution of the polymer with stirring over a period of several hours. The reaction mixture is then subjected to dialysis using Spectropor Membrane tubing (Mol. Wt. cutoff 6000–8000). Dialysis is continued for several days with frequent changes of water. In some cases the hydroxamic acid polymers precipitate from the organic reaction solvent during hydroxamation. In these cases the precipitated polymers are collected by filtration, dissolved in water, and dialyzed. The aqueous solutions were then filtered and freeze dried to give the dry polymer in the form of a flaky white solid.

Treatment Protocol

The bioassay was conducted on 6–7 week old male BDF$_1$ hybrid mice (16–20 g) obtained from Simonsen Laboratories Inc., Gilroy, Calif. and from Charles River Breeding Laboratoties, Ind., Kingston, N.Y.

The iron chelator screen essentially encompasses: (a) drug formulation, (b) attainment of some acute toxicity data, (c) hypertransfusion of mice with canine red blood cells, (d) a 7-day treatment interval, (e) daily collection of fecal and urinary pools, and (f) iron analysis and statistical evaluation of iron chelation efficacy. Each assay contains a non-transfused control group to document the effects of hypertransfusion in a second control group. With each assay, the proven clinically effective methane sulfonate salt of DFB, (Ciba Pharmaceutical Co.) is tested to provide a reference of relative potency of test compounds. Daily pools of urine and feces from each experimental group and each group are collected during the 7-day consecutive treatment period. Liver and spleen were dissected from mice deeply anesthetized with diethyl ether. Spleens and livers were blotted, weighed and homogenized. A gross pathological examination of major organs in situ is performed during necropsy. Iron analyses were subsequently conducted.

Results

All polymers synthesized during the course of this project were submitted to the Mason Research Instituted (MRI) for testing under approval by the NIADDKD. The structures and code numbers of the polymers and the results of the MRI screen are shown in Table II. The test results are given in terms of the average percent increase (+) or decrease (−) in the iron level of spleen, liver, feces, and urine for the mice receiving the drug to the same data for control mice hypertransfused, but receiving no drug.

The relative potency of a test drug is determined by comparing the percent iron changes for the drug with similar data obtained for DFB. The formula for calculating relative potency (P), is shown in Equation 1.

$$P = \frac{(S_{cx} + L_x + F_x + U_x)/\text{Dose}_x}{S_{Std} + L_{Std} + F_{Std} + U_{Std}/\text{Dose}_{Std}} \quad (1)$$

S, L, F and U are the absolute values of the average percent iron changes in spleen, liver, feces and urine, respectively. Subscripts x refer to the test drug and Std to the standard drug, DFB. To be included in this calculation the iron changes in spleen and liver must be negative, and the iron changes in feces and urine must be positive. If otherwise, the quantities are omitted from the calculation. In the cases of compounds 5b, 6b, 7b and 8b, the effect of dose size on bioactivity was also determined. These results are given in Table III.

On reviewing the considerable quantity of data now available on the many compounds tested, it is apparent that the most significant measure of the potency of the drug is the iron level in the urine. In the testing protocol, the percent iron change in spleen, liver, and feces are derived from small changes in materials normally fairly rich in iron. Rarely is the change more than 30% in the right direction; decrease for spleen and liver, increase for feces. Also the iron levels often vary widely with standard deviations up to 30% of the mean. On the other hand, iron levels in the urine can be increased by several hundred percent by only a moderately active iron chelator. Although standard deviations are still high, in the urine we see changes that are large and easily recognizable as significant in a material normally low in iron.

SYNTHESIS OF POLY(N-ACRYLOYL-β-ALANINE N'-METHYL HYDROXAMIC ACID)

N-ACRYLOYL-β-ALANINE

In a 1 1.3-necked round bottome flask an aqueous solution of sodium hydroxide was prepared by dissolving 96 gm NaOH (2.4 mole) in 200 ml distilled water. The solution was cooled to room temperature and 107.2 g β-alanine (1.2 mole) was dissolved. The mixture was cooled to below 0° C. (ice and salt mixture bath) and 97.2 ml freshly distilled acryloylchloride (1.2 mole) was added in small amounts from a dropping funnel while the temperature of reaction mixture was maintained strictly below 5° C. During the addition, the reaction mixture was stirred vigorously using a mechanical stirrer and after completing the addition, stirring was continued for another five minutes to allow the temperature to drop to 0° C. The reaction mixture was acidified to pH 4.0 (pHydrion paper) by addition of conc. HCl (about 45 ml). Solids were removed by filtration, and to the clear filtrate was added about 50 ml conc. HCl to attain pH 2.0. (During the addition of HCl, care should be taken to maintain temperture below 10° C.) The mixture was cooled to below 0° C. and the product crystallized out after one hour. After 2 hours of cooling to ensure complete precipitation of product, the reaction mixture was filtered and the product was dried overnight in a vacuum dessicator (Drierite) to obtain 111 gm (64.7% yield) of white crystals, mp 96° C.

N-ACRYLOYL-β-ALANINE BENZOTRIAZOLIDE

A 12 l. 3-neck round bottom flask was charged with 163 g benzotriazole (1.37 mole), 195.5 g N-acryloyl-β-alanine and 5 l. of commercial grade acetone. The mixture was stirred in an ice bath and 282 g of N,N'-dicyclohexylcarbodiimide (1.37 mole) was added. Stirring was continued overnight while the flask was kept in an ice bath and the precipitated dicyclohexylurea was removed by filtration (316 g, 1.41 mole). The clear filtrate was evaporated under vacuum (below 30° C.) until crystallization occurred. The solid was collected and the filtrate was again concentrated under vacuum to obtain more product. The combined product was washed with petroleum ether (32°–58° C.) followed by ethyl ether and air dried to yield 249 g pale yellowish compound. (75% yield) Mp. 118°–122° C.

The product obtained from acetone was washed immediately with petroleum ether and ether. Attempted air drying of product prior to washing resulted in a darkening of the yellow color of the product.

POLYMERIZATION OF N-ACRYLOYL-β-ALANINE BENZOTRIAZOLIDE AND CONVERSION TO THE HYDROXAMIC ACID POLYMER

Polymerization

Dimethylformamide (DMF) was purified by refluxing over phthalic anhydride and distilling. N-acryloyl-B-alaninebenzotriazolide (50 g, 0.205 mole) was dissolved in 150 ml DMF. The solution was deaerated thoroughly with argon for 30 minutes and 1 ml DMF solution containing 0.15 g AIBN initiator was added. Polymerization was conducted at 60° C. in argon atmosphere (surface deaeration only) for 20 hrs and 1 ml DMF solution containing 0.15 g AIBN was again added to polymerization mixture. Polymerization was continued for another 24 hrs and the solution was cooled to room temperature. The polybenzotriazolide was not isolated from DMF solution but the solution was used directly in the next step.

Hydroxamation

To a DMF solution (about 200 ml) containing 25 g CH$_3$NHOH·HCl (0.299 mole), was added triethylamine (41.7 ml, 0.299 mole). The mixture was stirred for 15 minutes and TEA·HCl 1 mole), was removed by filtration. The clear filtrate was added to half of the original polymer solutiion (100 ml containing 0.102 mole polybenzotriazolide) and the reaction was carried out at room temperature for 2 hours. The reaction mixture was again divided into two halves and worked up as follows:

The first half of the reaction mixture was transferred into spectrapor membrane tubing (mol. wt. cut off 6000–8000) and dialysed against water for 3 days. The aqueous solution of polymer was filtered, concentrated to 100 ml on the rotary evaporator at 60° C. and freeze dried to yield 8.75 g hydroxamic acid polymer for a 99% yield.

The second half of the reaction mixture was concentrated under high vacuum at 32°–34° C. and to the viscous polymer solution was added about 300 ml commercial grade acetone. The precipitated sticky polymer was washed with acetone, dissolved in methanol, precipitated by adding ether, dissolved again in methanol and reprecipitated with excess ether. The polymer was dissolved in 100 ml distilled water and the solution was freeze dried to yield (a) 7.5 g hydroxamic acid polymer.

The polymer is water soluble. Addition of iron to the aqueous solution gives the orange-red color of the iron complex. A mole ratio plot indicates that the complex forms 3:1 HA:Fe ratio.

The structural formulae of the compounds which are referenced at Tables I-III are listed below:

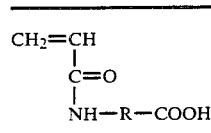
Compound 1

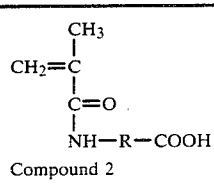
Compound 2

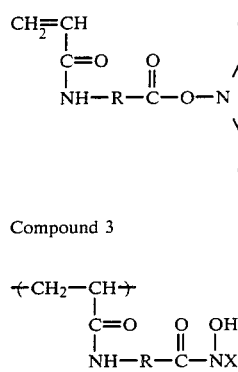
Compound 3

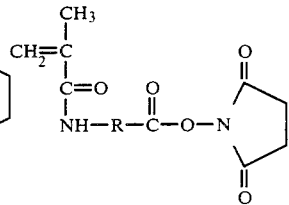
Compound 4

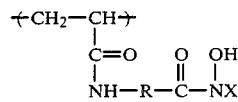
Compound 5 X = H
Compound 7 X = CH$_3$

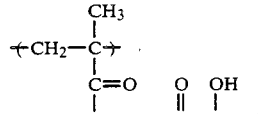
Compound 6 X = H
Compound 8 X = CH$_3$

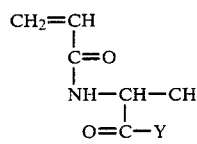
Compound 9 Y = OH
Compound 11 Y =

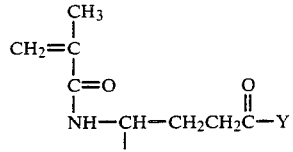
Compound 10 Y = OH
Compound 12 Y =

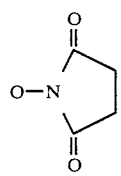

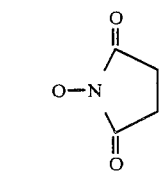

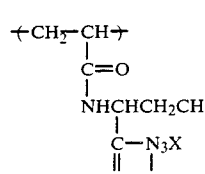

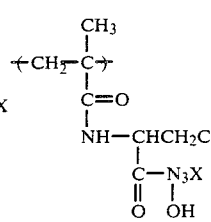

Compound 13 X = CH$_3$ $$CH_2=CH$$
$$|$$
$$C=O$$
$$|$$
$$O-N$$ (succinimide)

Compound 15

Compound 14 X = CH$_3$ $$\mathrm{+CH_2-CH+}$$
$$|$$
$$C=O$$
$$|$$
$$N-OH$$
$$|$$
$$X$$

Compound 16 X = H
Compound 17 X = CH$_3$

| R | | Amino acid spacer |
|---|---|---|
| a | —CH$_2$— | (gly) |
| b | —CH$_2$CH$_2$— | (β—ala) |
| c | DL-CH—<br>\|<br>CH$_3$ | (DL-ala) |
| d | L-CH—<br>\|<br>CH$_3$ | (L-ala) |
| e | DL-CH—<br>\|<br>CH<br>/ \<br>CH$_3$ CH$_3$ | (DL-val) |

TABLE I

CHARACTERIZATION OF MONOMERS AND MONOMER PRECURSORS PREPARED FOR THIS PROJECT

| No. | Yield % | mp Deg. C | mp (lit.) Deg. C | Ref. |
|---|---|---|---|---|
| 1a | 28% | 128 | 131 | 17 |
| 1b | 73% | 96–97 | 99 | 18 |
| 1c | 80% | 136–138 | 145 | 19 |
|  |  |  | (130-Ref. 9) |  |
| 1d | 84% | 158–160 |  |  |
| 2a | 78% | 102–104 | 104 | 14, 20 |
| 2b | 75% | 75–77 | 78 | 14, 21 |
| 2c |  | 112 | 118 | 22, 23, 24 |
|  |  | (102–104) |  |  |
| 2e |  | 86 | 102 | 22, 25 |
| 3a | 53% | 137 |  |  |
| 3b | 75% | 146 | 146 | 15 |
| 3c | 75% | 162 | 167 | 19 |
| 3d | 69% | 140–141 |  |  |
| 4a | 76% | 158–162 | 162 | 14 |
| 4b | 87% | 139–142 | 145 | 14, 21 |
| 4c |  | 116 |  |  |
|  |  | (135–138) |  |  |
| 4e |  | 199 |  |  |
| 9 |  | 118.5 | 118.5 | 23 |
| 10 |  | 130 | 130 | 23 |
| 11 |  |  |  |  |
| 12 |  |  |  |  |
| 15 |  |  |  |  |

TABLE II

EFFECTS OF HYDROXAMIC ACID POLYMERS ON HEPATIC, SPLENIC, FICIAL, AND URINARY IRON AND ON OVERALL POTENCY

| No. | Amino Acid Spacer | X | Dose mg/kg | Toxic[a] signs | % Fe Changes vs Controls Spleen | Liver | Feces | Urine | Potency |
|---|---|---|---|---|---|---|---|---|---|
| Desferrioxamine-B (Standard) | | | | | | | | | |
| — | — | — | 250 | None | ±2 | −23 | +7 | +270 | 1.0 |
| Acrylic Acid Series X = H | | | | | | | | | |
| 5a | gly | H | 500 | 3d, CNS ↓ BW ↓, S ↑ | +64 | +14 | −43 | −28 | 0 |
| 7a | gly | $CH_3$ | 500 | 2d, CNS ↓, S ↑ | −6 | +14 | −34 | −6 | 0 |
| 5c | DL ala | H | 500 | None | +43 | −13 | +9 | +35 | 0.1 |
| 7c | DL ala | $CH_3$ | 500 | None | 0 | +44 | +15 | +220 | 0.4 |
| 5d | L ala | H | 500 | S ↑, U ↓ | −19 | −17 | −12 | +252 | 0.7 |
| 5b | β ala | H | 500 | None | −38 | −34 | 0 | +873 | 1.6 |
| 7b | β ala | $CH_3$ | 500 | None | −35 | −40 | +15 | +786 | 1.5 |
| 13 | glu | $CH_3$ | 500 | 3d, CNS ↓, BW ↓, S ↑ | −36 | −19 | −45 | +98 | 0.4 |
| 16 | None | H | 250 | 1d, S ↑ | −5 | +3 | −62 | +58 | 0.2 |
| 17 | None | $CH_3$ | 350 | 5d, CNS ↓ | −46 | −6 | −80 | +73 | 0.3 |
| Methacrylic Acid Series X = $CH_3$ | | | | | | | | | |
| 6a | gly | H | 500 | None | +13 | +11 | +9 | +165 | 0.4 |
| 8a | gly | $CH_3$ | 500 | None | −12 | +11 | −6 | +162 | 0.4 |
| 6c | DL ala | H | 500 | None | +1 | −4 | +10 | +314 | 0.5 |
| 8c | DL ala | $CH_3$ | 400 | None | +4 | −3 | +22 | +178 | 0.5 |
| 8bI[b] | β ala | $CH_3$ | 500 | None | −2 | −11 | +17 | +212 | 0.5 |
| 8bII[c] | β ala | $CH_3$ | 500 | None | −41 | −49 | −3 | +331 | 0.9 |
| 8bIII[d] | β ala | $CH_3$ | 500 | None | −35 | −12 | −12 | +631 | 1.0 |
| 6b | ala | H | 500 | BW ↓ | −21 | +27 | −46 | +447 | 0.7 |
| 8e | DL val | $CH_3$ | 300 | None | +10 | −12 | −10 | +117 | 0.5 |
| 14 | glu | $CH_3$ | 500 | S ↑ | −22 | −27 | −12 | +121 | 0.4 |

[a] d, No. of deaths
CNS, Central Nervous System
BW, Body Weight
S, Spleen Weight
U, Urine Volume
↑ ↓, increase or decrease
[b] Intrinsic viscosity ($H_2O$) = 0.07
[c] Intrinsic viscosity ($H_2O$) = 0.92

TABLE III

EFFECT OF DOSE SIZE ON IN VIVO IRON REMOVAL AND POTENCY OF SEVERAL HYDROXAMIC ACID POLYMERS

| No. | Amino Acid Spacer | R | Dose mg/kg | Toxic signs | % Fe Changes vs Controls Spleen | Liver | Feces | Urine | Potency |
|---|---|---|---|---|---|---|---|---|---|
| 7b | β ala | $CH_3$ | 100 | None | +20 | −13 | −14 | +370 | 3.5 |
| | | | 200 | None | +6 | −14 | +6 | +426 | 2.0 |
| | | | 400 | None | −7 | −24 | −10 | +646 | 1.7 |
| | | | 800 | None | −9 | −41 | −15 | +892 | 1.6 |
| 6b | β ala | H | 75 | S | −12 | −6 | +5 | +71 | 1.2 |
| | | | 150 | S | +18 | +15 | −19 | +134 | 0.8 |
| | | | 300 | 6d, CNS, S | −30 | +8 | −57 | +104 | 0.4 |
| | | | 600 | 5d, CNS, BW | −49 | +9 | −60 | +164 | 0.5 |
| 8b | β ala | $CH_3$ | 150 | None | −41 | −29 | −8 | +82 | 0.9 |
| | | | 300 | None | −53 | −46 | −11 | +156 | 0.8 |
| | | | 600 | Weak | −38 | −37 | −4 | +205 | 1.0 |
| 5b | β ala | H | 200 | None | −5 | −17 | −6 | +349 | 1.7 |
| | | | 400 | None | −27 | −31 | −2 | +529 | 1.5 |
| | | | 600 | None | −38 | −34 | 0 | +873 | 1.6 |

We claim:

1. An iron chelator comprising a polymeric hydroxamic acid of the following general formula:

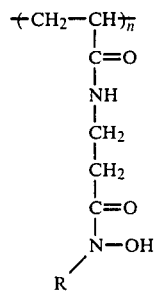

wherein R is hydrogen or lower alkyl and n is about 40 to about 300 or more.

2. The iron chelator of claim 1 wherein said lower alkyl is methyl.

3. A method of treating iron overload disorders comprising the administration to a patient in need of such treatment of a polymeric iron chelator having the general formula:

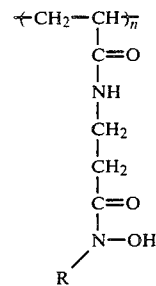

wherein R is hydrogen or lower alkyl and n is about 40 to about 300 or more, said iron chelator being administered in an amount sufficient to effect (a) the formation of a stable iron complex and (b) the metabolic elimination of excess iron from the plasma of the subject.

4. The method of claim 3 wherein said iron overload disorders are iron poisoning, hemochromotosis and transfusional hemosiderosis in Cooley's Anemia, sickle cell anemia, aplastic anemia and forms of leukemia.

5. The method of claim 3 wherein said polymeric iron chelator is administered in amounts from about 1 to about 5 g per day.

6. The method of claim 3 wherein said polymeric iron chelator is administered in amounts from about 20 to about 40 mg/kg/day.

7. The method of claim 3 wherein the lower alkyl is methyl.

8. The method of claim 3 wherein the subject is human or animal.

* * * * *